United States Patent [19]

De Bastiani et al.

[11] Patent Number: 4,604,997
[45] Date of Patent: Aug. 12, 1986

[54] ARTICULATED MINI EXTERNAL FIXATION DEVICE

[75] Inventors: Giovanni De Bastiani, Verona; Lodovico R. Brivio, Castenedola; Roberto Aldegheri, Lupatoto; Giovanni Faccioli, Monzambano, all of Italy

[73] Assignee: Orthofix S.r.l., Verona, Italy

[21] Appl. No.: 694,062

[22] Filed: Jan. 23, 1985

[30] Foreign Application Priority Data

Feb. 13, 1984 [IT] Italy ............................... 84909 A/84

[51] Int. Cl.$^4$ ............................................. A61F 5/04
[52] U.S. Cl. ............................ 128/92 A; 128/92 EB; 128/77
[58] Field of Search ............... 128/92 A, 92 R, 92 EB, 128/84 B, 77

[56] References Cited

U.S. PATENT DOCUMENTS 1,789,060  1/1931  Weisenbach .................. 128/92 A

FOREIGN PATENT DOCUMENTS 851028  3/1939  France .......................... 128/92 A
303453  2/1955  Switzerland .................. 128/92 A Primary Examiner—Gene Mancene
Assistant Examiner—C. W. Shedd
Attorney, Agent, or Firm—Hopgood, Calimafde, Kalil, Blaustein & Judlowe

[57] ABSTRACT

The invention contemplates orthopedic external mini-fixation apparatus comprising two articulated members having two clamps, each of which is carried by a different one of the articulated members. The articulating connection between members includes provision for simple and rapid alignment of the articulation axis with the articulation axis of the joint between two bones to be treated, thereby permitting early functional re-education and reduction of healing time. In its preferred form, several embodiments are disclosed.

17 Claims, 8 Drawing Figures

ARTICULATED MINI EXTERNAL FIXATION DEVICE

BACKGROUND OF THE INVENTION

The invention relates to orthopedic fixation devices, namely, minifixators, particularly adapted to controlled fixation and/or articulation of small bones, such as phalanges, metacarpal and metatarsal bones.

U.S. Pat. No. 4,312,336 describes a monolateral external fixation device having a variety of features designed to give the surgeon flexibility in applying the same to a number of bone-fixation situations, particularly involving large bones. But the relative complexity and bulk of the device make it inapplicable to fixation and/or articulation of small bones of the hand or foot. And a mere reduction in scale of the patented device would not meet the surgeon's requirements for simplicity, strength, bone anchorage, articulation and elongation, in a broken or otherwise defective small-bone situation.

BRIEF STATEMENT OF THE INVENTION

It is an object of the invention to provide an improved minifixator of the character indicated.

A specific object is to provide such a device with pin mounts adapted for articulated monolateral support of two spaced regions of small bone, as in conjunction with surgery of the hand or foot, as for arthrodesis, for axial deviations as well as in cases of hallux valgus, of metatarsus primus varus, for treatment of articular fractures, for inveterate luxations and subluxations in particular, for osteochondrytes, hallus rigidus and the like.

The invention achieves these objects with minifixation apparatus comprising two articulated members having two clamps, each of which is carried by a different one of the articulated members. The articulating connection between members includes provision for simple and rapid alignment of the articulation axis with the articulation axis of the joint between two bones to be treated, thereby permitting early functional re-education and reduction of healing time. In its preferred form, one of the articulated members ends in a fork and the other in a shank which is nested between arms of the fork; a hollow pin connects the members via aligned bores in the shank and fork ends. Each member has a clamp adapted for fixed connection to at least two bone-anchoring pins, and at least one of the clamps is longitudinally displaceable along the member by which it is carried. The hollow hinge pin is sized to accommodate through-passage and alignment of a Kirschner wire, for hinge-axis orientation and alignment with the axis of involved bone articulation, and the hinge pin is also so formed as to enable selective locking of a given angular relation between the articulated members.

DETAILED DESCRIPTION

Various embodiments of the invention will be described in conjunction with the accompanying drawings, in which.

Figure 1:
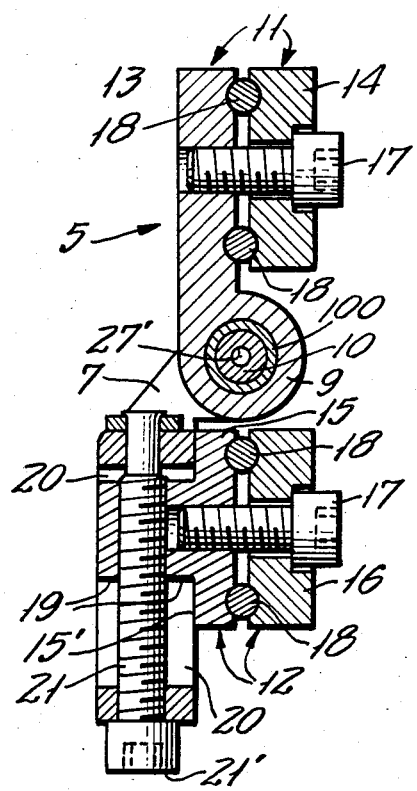
FIG. 1 is a side view of a preferred embodiment of an articulated minifixation device, shown in longitudinal section.
Figure 2:
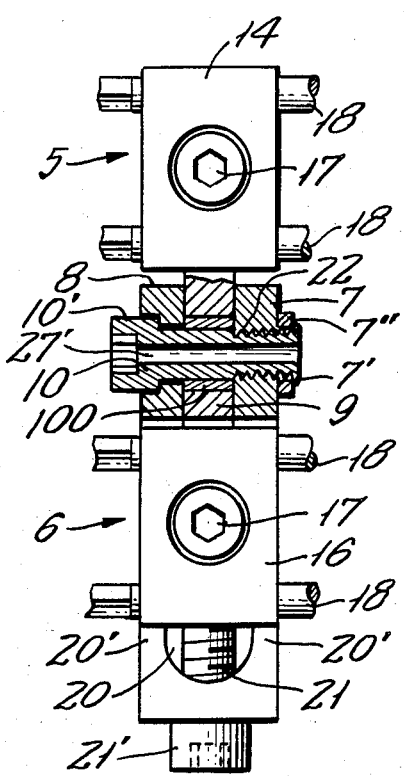
FIG. 2 is a plan view of the device of FIG. 1, partly broken away and in section at a plane which includes the articulation axis.

The external minifixation device of FIGS. 1 and 2 comprises two hinge-connected members 5-6, one (6) of which terminates in a fork with arms 7-8, and the other (5) of which terminates in a shank or blade 9 which is proportioned for stabilized fit between arms 7-8. Shank 9 is provided with a bushing 100 having a bore of diameter which corresponds to that of aligned bores in the fork arms or tynes 7-8, and a hollow hinge pin 10 completes the articulated connection. Pin 10 has a head 10' formed for wrench or screw-driver actuation, and head 10' is seated in a counterbore in arm 8. The other end of pin 10 is seen to protrude beyond arm 7 and a washer 7", and permanent retention is achieved by an outwardly conical flaring 7' of the end of the pin.

For many uses, it is sufficient for pin 10 to provide a freely articulating connection between members 5-6, in which case the described connection is adequate. But there are other situations in which it is desired to maintain a given angular setting of members 5-6 with respect to each other and therefore it is preferred to incorporate a lockable feature in the articulated connection. As shown in FIG. 2, this feature results from threads 22 on pin 10, engaged only to the threaded bore of arm 7. In this arrangement, wrench actuation at head 10' can determine whether or not arms 7-8 will be squeezed into locked engagement against the flanks of shank 9.

Each of the members 5-6 is formed to provide clamped engagement to at least two bone-anchoring pins. In the case of member 5, a first such clamp 11 comprises a jaw 13 integral with member 5, and a separate but cooperating jaw 14 which can be secured to jaw 13 as by wrenched actuation of a clamp screw 17. Mutually facing surfaces of jaws 5-6 are formed with spaced parallel cylindrically arcuate grooves, for reception and location of the shanks of two pins 18 therebetween. The shanks of pins 18 are cylindrical and are securely clamped in parallel relation, upon tightening screw 17 therebetween. And, preferably, a coplanar relation exists between the articulation axis of pin 10 and the axes of the clamped pins 18 of jaw 11.

In the case of member 6, a second clamp 12 is movably guided and comprises a base jaw 15 and a separate jaw 16. Jaws 15-16 have correspondingly grooved confronting faces and a single screw 17 therebetween, for secure clamping of two further pins 18.

For adjustably guided positioning of the movable clamp 12, the length of member 6 is characterized by a slot 20 extending between closed ends of member 6 and between spaced parallel sides or rails 20', and a downwardly extending carriage or guide block 19 integrally formed with jaw 15 is guided within and stabilized by sidewalls of slot 20. Block 19 has a threaded longitudinal bore, in constant engagement with a threaded rod or lead screw 21, and rod 21 is journaled in the respective closed ends of member 6, with access for wrenched rotary actuation via the suitably formed head 21' of rod 21. The axial location of rod 21 is stabilized by flaring the remote end of rod 21 over a washer, as shown in FIG. 1, and in the manner described at 7'–7" for pin 10 in FIG. 2.

It is apparent that adjusted rotation of rod 20 imparts longitudinal displacement to block 19 and thus also to the movable clamp 12 and its clamped pins 18. In such displacement, jaw 15 derives longitudinally extensive support from its continuous sliding engagement (at 15') with the spaced rails 20' of member 6, thus enabling maintenance of a preferred relation of coplanarity as between the hinge axis of pin 10 and the pins 18 held by clamp 12, whatever the adjusted displacement of clamp 12. And it will be understood that, if desired, a further clamp or locking feature (not shown) may be provided to retain an adjusted setting of lead screw 21.

In a very satisfactory embodiment of the invention, the overall length of arm 5 is 2.7-cm, and the longitudinal extent of adjustable arm 6 is 3.5-cm, from its outer or free end to its hinged end. Slot 20 is 2-cm long, and the section of slot 20 available for stabilized guidance of block 19 is a 0.8-cm square. Each of the clamps 11–12 is designed to secure two identical pins 18 at 1.2-cm spacing, and these pins are preferably self-perforating and self-threading standard cortical screws, e.g., 40×1.5 mm or 50×1.8 mm, having cylindrical shank diameters of 2.5 mm. The thread pitch on rod 14 is 20/cm, and the elongation span available for adjustable displacement of the movable clamp 12 is substantially 1-cm.

Figure 3:
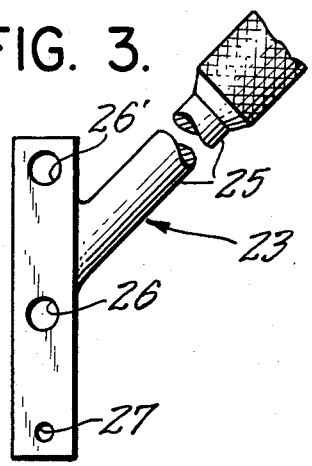
FIG. 3 is a plan view of a template tool, for use in applying the device of FIGS. 1 and 2 to bones of an afflicted joint.
Figure 4:
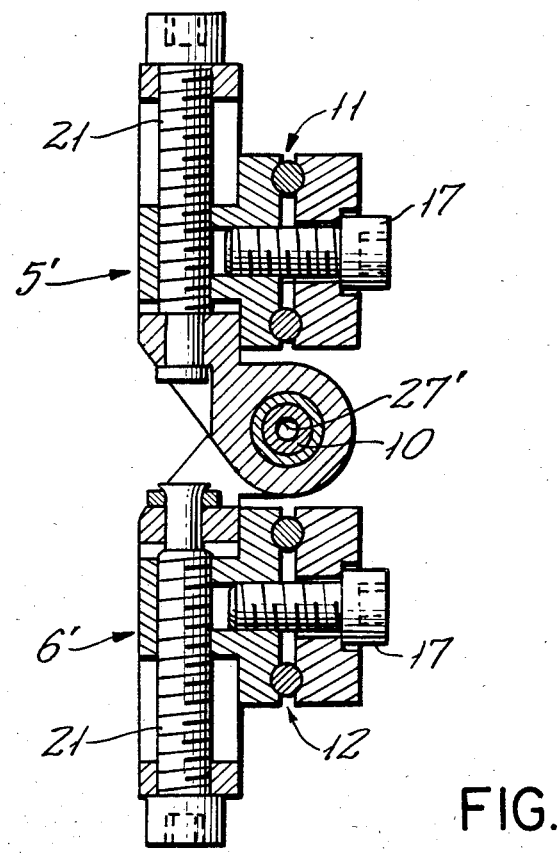

FIG. 3 is drawn alongside FIG. 2 and to the same scale, in order to illustrate a portable jig or template tool 23 whereby orthopedic pins 18 may be driven and set into one of the two articulated bones of a joint which is to be aided by the minifixator of FIGS. 1 and 2. Tool 23 comprises an elongate prismatic metal base 24 drilled at bores 26-26' for correctly spaced parallel guidance of the two pins 18 to be set by clamp 5, and drilled at bore 27 (with correct offset from bore 26) to match the bore 27' through articulation pin 10; an offset handle 25 facilitates tool manipulation. To apply the minifixation device of FIGS. 1 and 2, orthopedic pins 18, each having a self-tapping threaded end, are driven into the one bone, using the pointed end of a Kirschner wire at bore 27 to pin-point the articulation axis of the two involved bones, thus assuring a perfect alignment between the axis of rotation of the minifixator and that of the involved bones. When the first two pins 18 have been driven into the one bone, the clamp 11 of arm 5 is set to the driven pins 18; thereafter, the remaining pins 18 for clamp 12 are driven into the other bone of the joint, using the grooves of slightly relaxed jaws 15–16 as guides. When the pins 18 for clamp 12 have been thus driven into the other bone, the clamp 12 may be secured to its pins. The pins 18 for arm 6 need not be at the precise offset from the articulation axis that is required for arm 5, because, as noted above, clamp 12 is adjustable along slot opening 20. And if both of the clamps 11–12 are adjustable along their respective arms, it becomes even more easy to align the axis of minifixator articulation with that of joint articulation, in that both movable clamps can be longitudinally positioned, as may be independently required for each of them; the longitudinal section of FIG. 4 illustrates such a minifixator, wherein both clamps 11–12 are adjustably positionable along their respective arms 5'–6'.

Figure 5:
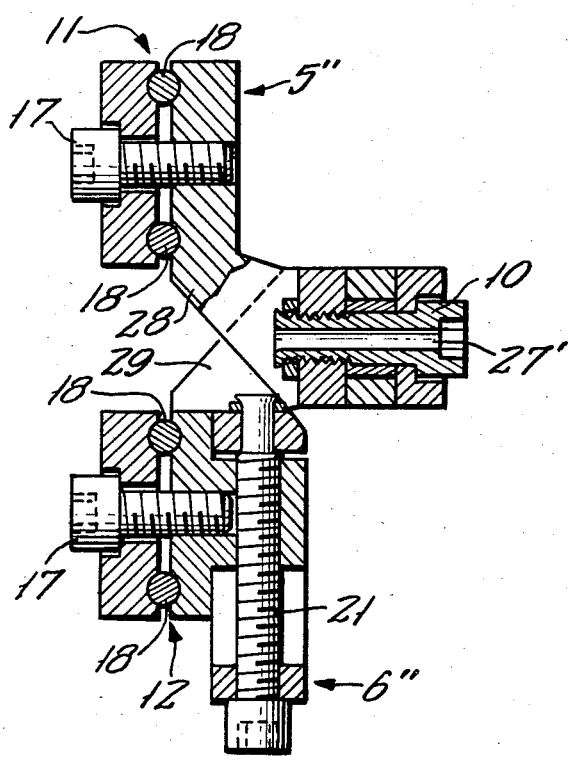
FIGS. 4 and 5 are views similar to FIG. 1, to show modifications.
Figure 6:
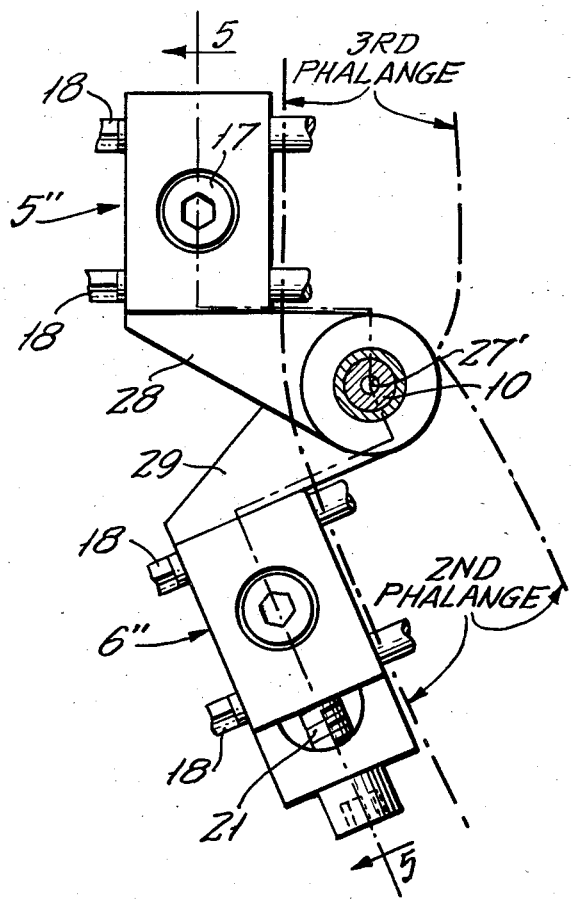
FIG. 6 is a view similar to FIG. 2, but applicable to the modification of FIG. 5.

FIGS. 5 and 6 illustrate a modification in which the respective clamps 11–12 of arms 5"–6" are rotatable about an articulation axis which is perpendicular to the plane of all the axes of the orthopedic pins 18. In FIG. 6, phantom outlines suggest a joint of second and third phalanges bones to which the device has been applied, it being noted that to avoid interference with the afflicted finger and to assure coincidence of the axis of articulation pin 10 with the articulation axis of the joint, there is a first component of axial offset (see FIG. 5) at segments 28–29 of the respective arms 5"–6" and a second component of radial offset (see FIG. 6) at the arm segments 28–29. And although only the clamp 12 of FIGS. 5 and 6 has been shown to be adjustable, it will be understood that an adjustable clamp 11 may be provided for arm 5" in the manner illustrated for arm 5' in FIG. 4.

The described constructions will be seen to achieve all stated objects, and the adjustably movable feature for one or both of the minifixator arms will be understood not only to facilitate a true accommodation of the minifixator-articulation axis to the joint-articulation axis, but also to enable a precise setting of distraction of the particular joint, as may be required for treatment of a particular affliction of the involved joint.

Although the invention has been described in detail for the disclosed specific forms, it will be understood that modifications may be made without departure from the scope of the invention. For example, although the context of description has been for a joint involving phalanges bones, it will be understood that the invention is not thus limited. The device is useful either for distraction of a joint or for the correction and fixation of a fracture, and (a) a metacarpal bone or (b) the joint between a metacarpal and the adjacent phalanges bone may be usefully served by the device.

Figure 7:
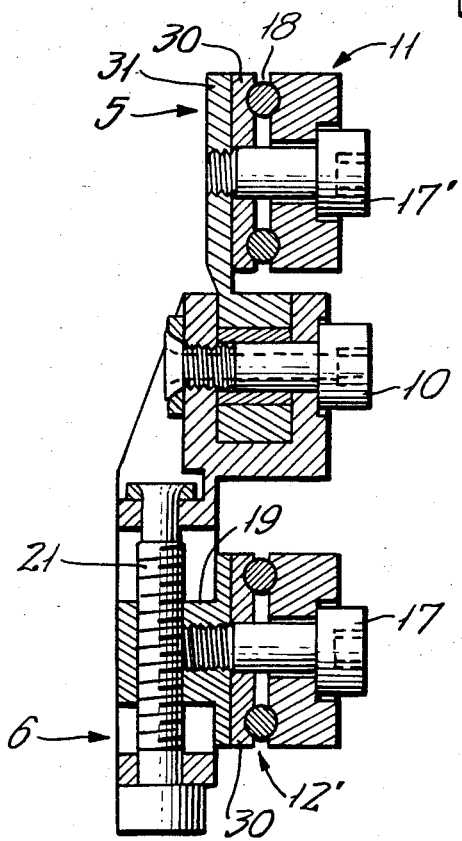
FIGS. 7 and 8 are views corresponding to FIGS. 1 and 2 but applicable to a further modification.
Figure 8:
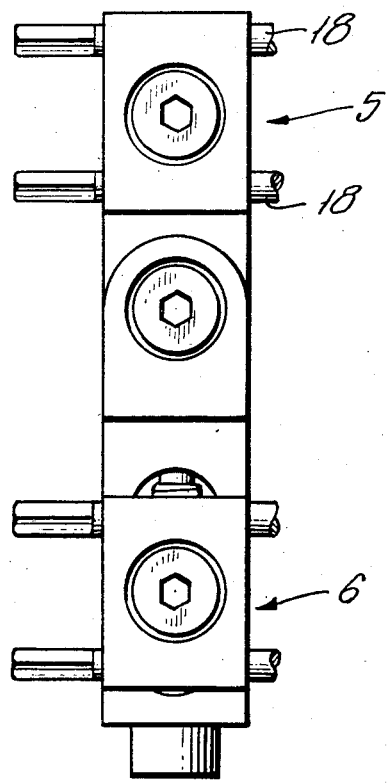

Also, by way of example, if minifixator articulation is not to be on the axis of joint articulation, FIGS. 7 and 8 illustrate a modification having great adaptability to external fixation of a broken bone. In FIGS. 7 and 8, the articulated arms 5–6 are essentially straight, i.e., they are not characterized by the offsets described at 28–29 for the arms of the structure of FIGS. 5 and 6. The hollow screw 10 is again the means of selectively clamping an articulated angular setting between arms 5–6, but the respective clamps 11'–12' incorporate the feature of selective rotation about the clamping axes of the respective clamp screws 17. To this end, for example in the case of the clamp 11', an intermediate jaw plate 30 is grooved for orthopedic-pin engagement, and the clamp screw 17 is threaded only to the base part 31 of arm 5. Thus, orthpedic pins 18 clamped at 11' may be at a desired angle to the elongation axis of arm 5. In similar fashion, the angular-adjustment feature of clamp 11' is seen also to be available for the longitudinally adjustable clamp 12', using another grooved swivel plate 30 which derives its support from the slide block 19.

What is claimed is:

1. An articulated external minifixator device, comprising two elongate arms with a single-axis articulating connection of adjacent ends of said arms, said connection being characterized by an alignment guide bore on the axis of articulation, first clamping means including spaced guideways adpated for clamping at least two orthopedic pins which are longitudinally spaced and oriented transverse to the direction of elongation of one of said arms, said first clamping means being at offset from the articulation axis, second clamping means including spaced guideways adapted for clamping at least two orthopedic pins which are longitudinally spaced and oriented transverse to the direction of elongation of the other of said arms, said second clamping means being at offset from the articulation axis, and means including a longitudinal lead screw in one of said arms and egaging the clamping means of said one arm for selective longitudinal positioning adjustment of the clamping means of said one arm.

2. The device of claim 1, in which the pin-supporting guideways of said clamping means are in spaced parallel relation, extending transversely of the involved arms.

3. The device of claim 2, in which the pin-supporting guideways are also parallel to the articulation axis.

4. The device of claim 2, in which the pin-supporting guideways extend on axes which are in a single geometrical plane, and in which the articulation axis is normal to said plane.

5. The device of claim 2, in which for each arm the pin-supporting guideways extend on axes which are in a geometrical plane which also includes the articulation axis.

6. The device of claim 1, wherein further clamping means coacting between said arms is selectively operable to fix an adjusted articulation angle between said arms.

7. The device of claim 1, wherein at said articulated connection between said arms, one of said arms is characterized by a forked end having spaced parallel tyne formations and the other of said arms is characterized by a shank received between the tyne formations of said one arm.

8. The device of claim 7, in which a hollow tubular pin is the means of articulated connection of said arms.

9. The device of claim 8, in which said tubular pin is headed at one end for referencing abutment with one of said tyne formations, said pin having threaded engagement to the other of said tyne formations and being free of threaded engagement to both said one tyne and said shank.

10. The device of claim 9, in which the other end of said tubular pin is flared for axial-retention within said other tynes.

11. The device of claim 10, in which a washer is interposed between said flared end and said other tyne.

12. The device of claim 1, in which said clamping means of said one arm comprises a base member having longitudinally guided engagement to said one arm, said base member having a jaw portion with spaced parallel guideways adapted to receive orthopedic pins, a further jaw member with cooperating guideways facing the guideways of said jaw portion, and a clamping screw between the guideways of said jaw portion and of said jaw member for clamping orthopedic pins between the respective cooperating guideways.

13. The device of claim 1, in which at least one of said clamping means comprises two plates each of which has two opposingly spaced parallel guideways adapted for orthopedic-pin engagement, and a clamping screw adapted to squeeze the jaw plates in clamped engagement upon two orthopedic pins in the guideways, the clamping screw having threaded engagement to a part of the involved arm, whereby a setting of the clamping means will retain the spaced relation of two orthpodeic pins in a selected angular relation about the axis of the clamping screw.

14. An articulated external miniflixator device, comprising two elongate arms with an articulating connection of adjacent ends of said arms, said connection being characterized by a single axis of articulation, first clamping means including spaced guideways adapted for clamping at least two orthopedic pins which are longitudinally spaced and oriented transverse to the direction of elongation of one of said arms, said first clamping means being at offset from the articulation axis, second clamping means including spaced guideways adapted for clamping at least two orthopedic pins which are longitudinally spaced and oriented transverse to the direction of elongation of the other of said arms, said second clamping means being at offset from the articualtion axis, and means including a longitudinal lead screw in one of said arms and engaging the clamping means of said one arm for selective longitudinal positioning adjustment of the clamping means of said one arm.

15. The device of claim 14, in which at least one of said clamping means comprises a jaw member having a clamping face with two spaced parallel guideways each of which is adapted to locate an orthopedic pin, said jaw member having a clamp-screw bore between said guideways and on an alignment prependicular to the geometirc plane of pins received in said guideways, and a clamping screw through the bore of said jaw member and engaged to a part of one of said arms for clamping of guideway-located pins between said jaw member and said part.

16. The device of claim 15, in which the arm part has two parallel pin-locating guideways at the same spacing as that of the jaw-member guideways.

17. The device of claim 15, in which the arm part has a flat surface perpendicular to the axis of clamping-screw engagement, said flat surface being of sufficient extent radially and circumferentially of said axis to provide reacting reference for clamping two orthopedic pins at any selected angle of pin orientation about said axis of clamp-screw engagement.

* * * * *